(12) United States Patent
Dabney (10) Patent No.: US 10,350,653 B1
(45) Date of Patent: Jul. 16, 2019

(54) METHOD, SYSTEM AND DEVICE FOR REDUCING MICROBIAL CONCENTRATION AND/OR BIOFILM FORMATION

(71) Applicant: DABNEY PATENTS, L.L.C., Georgetown, TX (US)

(72) Inventor: Paul Dabney, Georgetown, TX (US)

(73) Assignee: DABNEY PATENTS, L.L.C., Georgetown, TX (US)

( * ) Notice: Subject to any disclaimer, the term of this patent is extended or adjusted under 35 U.S.C. 154(b) by 0 days.

(21) Appl. No.: 16/014,406

(22) Filed: Jun. 21, 2018

(51) Int. Cl.
 *A61L 2/10* (2006.01)
 *B01J 19/12* (2006.01)
 *B08B 7/00* (2006.01)
 *B08B 17/00* (2006.01)

(52) U.S. Cl.
 CPC .............. *B08B 7/0057* (2013.01); *A61L 2/10* (2013.01); *B01J 19/123* (2013.01); *B08B 17/00* (2013.01)

(58) Field of Classification Search
 CPC ...... B08B 7/0057; B08B 17/00; B01J 19/123; A61L 2/10; E21B 21/068; C02F 2305/02; C02F 2305/023
 See application file for complete search history.

(56) References Cited

U.S. PATENT DOCUMENTS

| | | | |
|---|---|---|---|
| 2013/0023448 A1* | 1/2013 | Glasscott | C02F 9/00 507/100 |
| 2017/0030508 A1* | 2/2017 | Pilloni | B05D 7/222 |

* cited by examiner

*Primary Examiner* — Lucas A Stelling
(74) *Attorney, Agent, or Firm* — Maier & Maier, PLLC (57) ABSTRACT

Described herein are various methods, systems, and apparatus for reducing and eliminating biofilms from hydrocarbons. A combination of oxidizing agents and radiation of certain wavelengths forms a synergistic reaction. The synergistic reaction generates EMODs, which are effective in reducing microbial count and eliminating or blocking biofilm formation, particularly in anaerobic environments. This synergistic reaction has a relationship to EMOD creation and has a detrimental effect on Microbial Contamination (MC), Microbial Influenced Corrosion (MIC) and biofilm creation. MC, MIC and biofilm can be eliminated or greatly reduced with the treatment methods in or on equipment including pipelines, storage tanks, and refinery processing equipment.

12 Claims, 3 Drawing Sheets

METHOD, SYSTEM AND DEVICE FOR REDUCING MICROBIAL CONCENTRATION AND/OR BIOFILM FORMATION

BACKGROUND

The phenomena of microbiological contamination of the oil and/or natural gas environment represent a broad problem. Microbial Contamination (MC) and Microbial Influenced Corrosion (MIC) both pose severe operational, environmental, and safety problems to the petroleum and/or natural gas industries, particularly with respect to degradation of the hydrocarbon products and corrosive damage of equipment used in the storage, processing, and/or transport of hydrocarbon products such as oil, gas, crude and/or processed materials.

First, the degradation of petroleum hydrocarbons is associated with the negative effect of microorganisms. The microbes use hydrocarbons contained in crude, oil and/or gas as a source of carbon and change the properties of this crude, oil and/or gas, thus reducing its value. For example, the changes in oil density, sulfur content and viscosity cause disruption in oil extraction and processing technology, bring about significant economic losses and cause adverse environmental effects. Industry research indicates that 10%-14% of oil and gas is lost due to Microbial Contamination.

Second, in addition to lowering the content of hydrocarbons in crude, oil and/or gas, problems also concern the ways crude, oil, natural gas and/or other petroleum products is stored, products of its processing, and drilling fluids. The adverse activity of microorganisms causes corrosion of transmission installations (e.g., oil or gas pipelines), producing undesirable substances (including $H_2S$, polymers, organic acids, etc.) that affect the performance of oil and gas. Costs resulting from MC and MIC and biofilm formation in these industries occur due to repair and replacement of damaged equipment, spoiled oil, environmental clean-up, and injury-related health care, amount to well over several billion USD per year.

A variety of strategies have been developed to mitigate the negative effects of MC, MIC and/or the biofilms that contribute or cause MC and MIC. Such techniques include the use of corrosion resistant metals, temperature control, pH control, radiation, filtration, protective coatings with corrosion inhibitors, chemical controls (e.g., biocides, oxidizers, acids, alkalis), bacteriological controls (e.g., phages, enzymes, parasitic bacteria, antibodies, competitive microflora), pigging (i.e., mechanical delamination of corrosion products), anodic and cathodic protection, and modulation of nutrient levels. Attempts to eliminate microorganisms typically involve using chemicals exhibiting biocidal properties, which besides the physical methods is the most popular and most effective technique of eliminating Microbiological Contamination, Microbiological Influenced Corrosion and biofilm formation. However, the selection of appropriate antibacterial or antifungal agents requires the consideration of factors affecting the efficiency of the process. In fact, each of these existing methods face obstacles, such as, high cost, lack of effectiveness, short life-span, or requirement for repeat applications. For example, regular biocide injections are only effective sometimes and only in particular environments. In addition, biocides often fail due to incompatibility with other commonly used corrosion inhibitors and because of biofilm permeability issues, i.e., the biocides are unable to penetrate or permeate the biofilms due to the properties of the extracellular matrix of the biofilms. In addition, many of the above controls are not practical for implementing in the oil field due to the potential effect on the downstream processes.

In the oil field, pigging and biocides are the most commonly used approaches for controlling biofilms and corrosion. Pigging is required to remove or disrupt the biofilm on the pipe surfaces. Pigging can also remove many of the harmful iron sulfide deposits. While pigging will be substantially effective where thick biofilms are present, thin biofilms and thin iron sulfide deposits are not appreciably affected by the scraping action of pigs. Subsequently, biocides and surfactant biocide treatments are used extensively to control bacterial activity in oil field systems. However, biocides are not typically effective in penetrating the biofilms, and therefore, have reduced effectiveness against the underlying bacteria. Combination treatments in conjunction with pigging are more effective than the chemical treatments alone. However, treatments must be made routinely on a fixed schedule or else the bacteria population increases significantly, and control becomes even more difficult.

Thus, there exists a need in the art for an improved approach for inhibiting microbial concentration and/or biofilm formation that avoids the above indicated problems associated with existing methods, and in particular, which effectively reduces, mitigates, or otherwise eliminates Microbial Contamination, Microbial Influenced Corrosion and/or associated biofilms in/on oil and gas refinery equipment.

SUMMARY

Various methods, systems and devices for reducing microbial concentration in a hydrocarbon or for reducing biofilms formed in a hydrocarbon, on the surface of the hydrocarbon, or on the surface of equipment involved in the storage, transport or processing of the hydrocarbon may be shown and described herein. The methods, systems and devices may find application in the oil and/or natural gas production industries, more particularly, for mitigating or eliminating microbial contamination (MC) in hydrocarbons, microbial influenced corrosion (MIC) on metal surfaces, and/or creation and activity of biofilms.

Exemplary embodiments relate, in part, to a discovery that oxidizing chemicals, together with radiation of certain wavelengths, form a synergistic reaction generating electrically modified oxygen derivatives (EMODs). Prior to the disclosure, this synergistic reaction involving oxidizing agents and radiation of certain wavelengths was not known or appreciated as to its connection with EMOD creation or its effects on elimination or mitigation of MC, MIC or biofilm creation.

The resulted synergistic reaction may significantly reduce microbial concentration and biofilms on surfaces and in solutions, and, consequently, may be used to reduce, mitigate, or eliminate microbial contamination (MC) in hydrocarbons and/or microbial influenced corrosion (MIC) on metal surfaces, in particular, metal surfaces of equipment involved in the storage, transport, and refinement of petrochemicals in the oil and natural gas industries. Experiments have demonstrated that the combined synergistic reaction is over 300 percent more effective in elimination of MC, MIC and/or biofilm formation than either the oxidizing chemicals or the radiation if acting individually.

In one aspect, a method for reducing microbial concentration in a hydrocarbon or for reducing biofilms formed in a hydrocarbon, on the surface of the hydrocarbon, or on the surface of equipment involved in the storage, transport or processing of the hydrocarbon may be provided. The method may include introducing an effective amount of a liquid composition having an oxidizing agent compound or a functionally equivalent analog or derivative thereof into the hydrocarbon to be treated and then exposing the resulted mixture of the hydrocarbon and the liquid composition to radiation of certain wavelengths. The liquid composition comprising the oxidizing agent compound or a functionally equivalent analog or derivative thereof may function together with the radiation of certain wavelengths to lead to a synergistic reaction creating EMODs, thereby reducing or eliminating microbes and the biofilm and/or sludge that they produce.

In another aspect, a combination for reducing microbial concentration in a hydrocarbon or for reducing biofilms formed in a hydrocarbon, on the surface of the hydrocarbon, or on the surface of equipment involved in the storage, transport or processing of the hydrocarbon may be provided. The combination may include a liquid composition having an oxidizing agent compound or a functionally equivalent analog or derivative thereof, and radiation of certain wavelengths. The liquid composition including the oxidizing agent compound or a functionally equivalent analog or derivative thereof may function together with the radiation of certain wavelengths to lead to a synergistic reaction creating EMODs, thereby reducing or eliminating microbes and the biofilm and/or sludge that they produce.

In still another aspect, a device for reducing microbial concentration in a hydrocarbon or for reducing biofilms formed in a hydrocarbon, on the surface of the hydrocarbon, or on the surface of equipment involved in the storage, transport or processing of the hydrocarbon may be provided. The device may include an oxidizing agent introducing component and a radiation emitting component. The oxidizing agent introducing component may be adapted to introduce a liquid composition an oxidizing agent compound or a functionally equivalent analog or derivative thereof to the hydrocarbon to be treated. The radiation emitting component may be adapted to emit or create radiation of certain wavelengths. The liquid composition comprising the oxidizing agent compound or a functionally equivalent analog or derivative thereof may function together with the radiation of certain wavelengths to lead to a synergistic reaction creating EMODs, thereby reducing or eliminating microbes and the biofilm and/or sludge that they produce.

In certain embodiments, the radiation of certain wavelengths may be radiation of a wavelength between 300 nanometers and 600 nanometers.

In certain embodiments, the effective amount of the liquid composition may provide the minimal amount of the oxidizing agent compound or a functionally equivalent analog or derivative thereof which results in a measurable or detectable effect on the microbial concentration or the biofilm formation.

In certain embodiments, the effective amount of the liquid composition may provide a concentration of the oxidizing agent compound or a functionally equivalent analog or derivative thereof that is between about 0.001 percent to 50 percent or more of the volume of the hydrocarbon to be treated.

In certain embodiments, the effective amount of the liquid composition comprising the oxidizing agent compound or a functionally equivalent analog or derivative thereof may be determined on the basis of any one or more of the density and light absorbing quality of the hydrocarbon to be treated, and the size and shape of the container thereof.

In certain embodiments, the oxidizing agent compound may be hydrogen peroxide, urea, carbamide peroxide, or benzoyl peroxide.

In certain embodiments, the formulation of the liquid composition may be determined on the basis of whether the hydrocarbon to be treated is under aerobic or anaerobic conditions, pH of the hydrocarbon, salinity of the hydrocarbon, consortium or population characteristics of the microorganism present in the hydrocarbon, the microbial content of the hydrocarbon and/or the microbial content of the biofilms.

In certain embodiments, the liquid composition comprising the oxidizing agent compound or a functionally equivalent analog or derivative thereof may further include at least one other inhibitor against microbial contamination in a hydrocarbon and/or microbial influenced corrosion on a metal surface.

In certain embodiments, the at least one other inhibitor may be a biocide selected from a group of germicides, antibiotics, antibacterials, antivirals, antifungals, antiprotozoals and antiparasites.

In certain embodiments, the wavelength, intensity, duration time and/or location relative to the hydrocarbon to be treated, of the radiation, may be determined on the basis of any one or more of the density and light absorbing quality of the hydrocarbon, the size and shape of the container thereof, whether the hydrocarbon is under aerobic or anaerobic conditions, pH of the hydrocarbon, salinity of the hydrocarbon, consortium or population characteristics of the microorganism present in the hydrocarbon, and the microbial content of the biofilms.

In certain embodiments, a secondary treatment may be carried out for reducing microbial concentration or biofilm formation, which may be selected from the group consisting of pigging, sonicization, radiation, filtration, stirring, bacteriological control, chemical control, temperature control, pH adjustment, nutrient adjustment, anodic and cathodic protection, protective coating with corrosion inhibitors, and installation of corrosion resistant metals.

In certain embodiments, the microbial concentration or the biofilms may be associated with fungi.

In certain embodiments, the microbial concentration or the biofilms may be associated with aerobic bacteria.

In certain embodiments, the microbial concentration or the biofilms may be associated with anaerobic bacteria.

In certain embodiments, the anaerobic bacteria may be selected from the group of sulfate-reducing bacteria, iron-oxidizing bacteria, sulfur-oxidizing bacteria, nitrate reducing bacteria, methanogens, and acid producing bacteria. The sulfate-reducing bacteria may be of the genera *Desulfovibrio, Desulfotomaculum, Desulfosporomusa, Desulfosporosinus, Desulfobacter, Desulfobacterium, Desulfobacula, Desulfobotulus, Desulfocella, Desulfococcus, Desulfofaba, Desulfofrigus, Desulfonema, Desulfosarcina, Desulfospira, Desulfotalea, Desulfotignum, Desulfobulbus, Desulfocapsa, Desulfofustis, Desulforhopalis, Desulfoarculus, Desulfobacca, Desulfomonile, Desulfotigmum, Desulfohalobium, Desulfomonas, Desulfonatronovibrio, Desulfomicrobium, Desulfonatronum, Desulfacinum, Desulforhabdus, Syntrophobacter, Syntrophothermus, Thermaerobacter*, and *Thermodesulforhabdus*.

In certain embodiments, the susceptible metal surface may be a metal surface of equipment for refining, storing, or transporting of crude, oil, gas or other raw materials or processed products. Such equipment may be, for example, metal (e.g., steel) pipelines, storage containers, and refinery processing equipment.

In certain embodiments, the liquid composition including the oxidizing agent compound or a functionally equivalent analog or derivative thereof may be an aqueous composition.

In certain embodiments, the liquid composition including the oxidizing agent compound or a functionally equivalent analog or derivative thereof may be a non-aqueous composition.

In certain embodiments, the liquid composition including the oxidizing agent compound or a functionally equivalent analog or derivative thereof may have an acidic pH, ranging from about 6.0-7.0, to about 5.5-6.5, to about 4.5-5.5, to about 3.5-4.5, to about 2.5-3.5, to about 1.5-2.5, or lower than 1.5.

In other embodiments, the liquid composition including the oxidizing agent compound or a functionally equivalent analog or derivative thereof may have a basic pH, ranging from about 7.0-7.5, to about 7.5-8.5, to about 8.5-9.5, to about 9.5-10.5, to about 10.5-11.5, to about 11.5-12.5, to about 12.5-13.5 to about 14.

In still other embodiments, the liquid composition including the oxidizing agent compound or a functionally equivalent analog or derivative thereof may have a neutral pH, ranging from about 6-8, or about 6.5-7.5, or about 6.7-7.3, or about 6.8-7.2, or about 6.9-7.1, or about 7.

In still other embodiments, the pH of the aqueous environment of or surrounding the hydrocarbon and/or its derivatives to be treated may be adjusted with buffers or other pH-altering agents to adjust the pH to any basic, neutral, or acidic conditions.

In certain embodiments, the effective amount of the liquid composition comprising the oxidizing agent compound or a functionally equivalent analog or derivative thereof may be deposited in the water that exists where the hydrocarbon is collected, stored or transported. Recognizing that the microbes require water to survive and multiply, treating the water with the oxidizing agent while exposing the mixture to radiation of certain wavelengths may create EMODs that reduce or eliminate the MC, MIC and/or biofilm.

The exemplary methodologies shown and described herein can provide numerous advantageous over existing mitigation practices, such as, but not limited to:

(a) the oxidizing agent may be a natural product of environmental bacteria, hence minimal environmental impact compared to currently available biocides;

(b) in existing methods, biocides are naturally taken up by bacteria in a biofilm and induce a switch to planktonic growth behavior (i.e., growth away from biofilm environment) and thus, lack biofilm permeability aspects needed to better eliminate MC and MIC;

(c) this MC and MIC eliminating or reducing treatment may be compatible with commercial corrosion inhibitors, whereas many current biocides are not;

(d) the synergistic reaction between the oxidizing agent and the radiation which produces EMODs presents no negative environmental impact, which is unique compared with current methods of treating MC and MIC, and thus this invention results in a more complete elimination or reduction in MC and MIC than currently available methods; and (e) the reduction in MC and MIC by the method disclosed in the invention is significantly greater than that by currently available methods.

BRIEF DESCRIPTION OF THE DRAWINGS

Advantages of exemplary embodiments of the method, combination and device for reducing microbial concentration or biofilm formation will be apparent from the following detailed description of the exemplary embodiments. The following detailed description should be considered in conjunction with the accompanying figures in which.

DETAILED DESCRIPTION

Aspects of the present invention are disclosed in the following detailed description and related figures directed to specific exemplary embodiments of the invention. Those skilled in the art will recognize that alternative exemplary embodiments may be devised without departing from the spirit or the scope of the claims. Additionally, well-known elements of exemplary embodiments of the invention will not be described in detail or will be omitted so as not to obscure the relevant details of the invention.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage, or mode of operation.

Unless defined otherwise, all technical and scientific terms used herein have the meaning commonly understood by a person skilled in the art to which this disclosure belongs. The following terms may have meanings ascribed to them below, unless specified expressly otherwise. However, it should be understood that other meanings that are known or understood by those having ordinary skills in the art are also possible, and within the scope of the present disclosure.

As used herein, the term "biocide" refers to a chemical substance or microorganism which can deter, render harmless, or exert a controlling effect on any harmful organism by chemical or biological means. Biocides include not just those that are synthetic, but also those that are naturally obtained, e.g., obtained or derived from bacteria and plants. Biocides can include, but are not limited to, germicides, antibiotics, antibacterials, antivirals, antifungals, antiprotozoals and antiparasites. Such compounds that can be used as biocides are well known in the art and may be obtained easily from commercial sources.

As used herein, the terms "Microbial Contamination" (or "MC") and "Microbial Influenced Corrosion" (or "MIC"), or similar terms, are well known terms in the art and shall be understood according to the meaning ascribed in the field. In other words, MC and MIC mean contamination of hydrocarbons and corrosion to metal surfaces caused directly or indirectly through the effects of bacteria and their byproducts and metabolites, including especially bacteria that grow on the metal surface in a biofilm. Both MC and MIC can occur in both aerobic and anaerobic conditions and generally are thought to at least require the presence of bacteria in a biofilm. MC is considered "biotic contamination." MIC is considered "biotic corrosion." MC is also associated with sludge formation in hydrocarbons resulting from the growth of microbes in the hydrocarbons or in the water associated with the hydrocarbons. MIC is also associated with surface pitting, which leads to more rapid corrosive failure than uniform corrosion.

As used herein, the term "corrosion associated biofilms" refers to biofilms that have corrosive properties which contribute to Microbial Influenced Corrosion.

As used herein, the term "corrosion" refers to the general deterioration of a material (e.g., metallic material) due to its reaction with the environment.

As used herein, the term "oxidizing agent" refers in chemistry to a substance that has the ability to oxidize other substances—in other words to cause them to lose electrons. Typical oxidizing agents include oxygen, hydrogen peroxide and the halogens. In one sense, an oxidizing agent is a chemical species that undergoes a chemical reaction that removes one or more electrons from another atom. In that sense, it is one component in an oxidation-reduction (redox) reaction. In the second sense, an oxidizing agent is a chemical species that transfers electronegative atoms, usually oxygen, to a substrate.

As used herein, "oxidizing agent equivalent" or "oxidizing analog or functionally equivalent compound, molecule or derivative" or similar terms include any known or yet unknown compounds that have a structure that is similar to oxidizing agents to a degree such that they can produce the same or similar biological effects as oxidizing agents.

Common oxidizing agents (O-atom transfer agents) may include, but are not limited to: (1) oxygen ($O_2$), (2) ozone ($O_3$), (3) hydrogen peroxide ($H_2O_2$) and other inorganic peroxides, Fenton's reagent, (4) fluorine ($F_2$), chlorine ($Cl_2$) and other halogens, (5) nitric acid ($HNO_3$) and nitrate compounds, (6) sulfuric acid ($H_2SO_4$), (7) peroxydisulfuric acid ($H_2S_2O_8$), (8) peroxymonosulfuric acid ($H_2SO_5$), (9) chlorite, chlorate, perchlorate, and other analogous halogen compounds, (10) hypochlorite and other hypohalite compounds, including household bleach (NaClO), (11) hexavalent chromium compounds such as chromic and dichromic acids and chromium trioxide, pyridinium chlorochromate (PCC), and chromate/dichromate compounds, (12) permanganate compounds such as potassium permanganate, (13) sodium perborate, (14) nitrous oxide ($N_2O$), nitrogen dioxide ($NO_2$), dinitrogen tetroxide ($N_2O_4$), (15) potassium nitrate (KNO3), the oxidizer in black powder, (16) sodium bismuthate, and (17) urea.

As used herein, the term "radiation" refers in physics to the emission or transmission of energy in the form of waves or particles through space or through a material medium. This includes, but is not limited to: (1) electromagnetic radiation, such as radio waves, microwaves, ultraviolet light, visible light, x-rays, and gamma ($\gamma$) radiation, (2) particle radiation, such as alpha ($\alpha$) radiation, beta ($\beta$) radiation, and neutron radiation (particles of non-zero rest energy), (3) acoustic radiation, such as ultrasound, sound, and seismic waves (dependent on a physical transmission medium), and (4) gravitational radiation, radiation that takes the form of gravitational waves, or ripples in the curvature of spacetime.

The word "radiation" arises from the phenomenon of waves radiating (i.e., traveling outward in all directions) from a source. This aspect leads to a system of measurements and physical units that are applicable to all types of radiation. Because such radiation expands as it passes through space, and as its energy is conserved (in vacuum), the intensity of all types of radiation from a point source follows an inverse-square law in relation to the distance from its source. Like any ideal law, the inverse-square law approximates a measured radiation intensity to the extent that the source approximates a geometric point. Some of the ultraviolet spectrum that begins above energies of 3.1 eV, a wavelength less than 400 nm is non-ionizing, but is still biologically hazardous due to the ability of single photons of this energy to cause electronic excitation in biological molecules, and thus damage them by means of certain reactions. This property gives the ultraviolet spectrum some of the properties of ionizing radiation in biological systems without actual ionization occurring. In contrast, visible light and longer-wavelength electromagnetic radiation, such as infrared, microwaves, and radio waves, consists of photons with too little energy to cause damaging molecular excitation. Light, or visible light, is a very narrow range of electromagnetic radiation of a wavelength that is visible to the human eye, or 380-750 nm which equates to a frequency range of 790 to 400 THz respectively. More broadly, physicists use the term "light" to mean electromagnetic radiation of all wavelengths, whether visible or not.

As used herein, the term "sulfate-reducing bacteria" or "SRB," which are considered one of the main culprits of biotic contamination and biotic corrosion in anaerobic conditions, are a grouping of bacteria that includes at least 220 species which produce $H_2S$ and use sulfates as the terminal electron acceptor. Most SRB are considered obligate anaerobes, meaning that the cells cannot metabolize and/or replicate in the presence of oxygen, although many species can temporarily tolerate low levels of oxygen. Furthermore, anaerobic conditions capable of supporting SRB growth can be created in overall aerobic environments, due to the micro-niches created within the bacterial biofilm/corrosion product layer. Although SRB are the most studied and well understood of the anaerobic corrosion inducing bacteria, both MC and MIC can occur in anaerobic conditions in the absence of SRB.

As used herein, the term "pigging" refers to a well-known process of intentional mechanical delaminating corrosion products and/or biofilm material from metal surfaces.

As used herein, the singular forms "a", "an", and "the" include plural references unless the context clearly dictates otherwise. All numerical values within the detailed descriptions and the claims herein are modified by "about" or "approximately" the indicated value and take into account experimental error and variations that would be expected by a person having ordinary skills in the art.

Reference will now be made in detail to exemplary embodiments of the disclosure. In certain exemplary embodiments, and generally referring to FIGS. 1-3, a system, device and method of reducing microbial concentration in a hydrocarbon or for reducing biofilms formed in a hydrocarbon, on the surface of the hydrocarbon, or on the surface of equipment involved in the storage, transport or processing of the hydrocarbon may be shown and described. It will be appreciated that this disclosure provides an effective and cost-efficient solution to solve the problem of microbial contamination (MC) in a liquid composition comprising crude, oil, gas, their derivatives or a functionally equivalent analog or derivative and water. Also provided may be a solution to solve the problem of Microbial Influenced Corrosion (MIC) on solid surfaces, such as surface of the equipment used in the petroleum and natural gas industries to store, transport, and process raw or refined materials (e.g., crude, oil, gas and other processed products). Additionally, this disclosure may provide an effective and cost-effective solution for preventing and/or mitigating the formation of harmful biofilms associated with Microbial Contamination and/or Microbial Influenced Corrosion of metal surfaces of oil and gas production, storage, and transport equipment.

While the disclosure will be described in conjunction with the exemplary embodiments, one skilled in the art can understand that it is not intended to limit the disclosure to those embodiments. Any combination, devices or methods provided herein can be combined with one or more of any of the other combination, devices and methods provided herein. To the contrary, this invention is intended to cover alternatives, modifications, and equivalents as may be included within the spirit and scope of the disclosure as defined by the appended claims.

Penetration and Development of Microorganisms

Microorganisms may penetrate into oil fields as a result of drilling, and/or into oil and fuel storage tanks, oil pipelines and transmission facilities, which are the perfect place for colonization by both aerobic and anaerobic microorganisms. The stages during which microorganisms may emerge are commonly: (1) stage of application of drilling fluids, which may be contaminated in this way allochthonous bacteria are introduced to the deposit, (2) stage of supply—borehole watering with highly contaminated water, (3) stage of oil transport—presence of microorganisms in contaminated water in transmission systems, (4) petroleum processing stage, and (5) stage of storage of crude oil and its processing products. It is extremely difficult to prevent microbiological contamination because it is impossible to maintain sterile conditions during the extraction, transport and storage of crude oil. In fact, at each stage of oil processing from its exploitation, transport, processing and ending with the storage, it can be subjected to the action of microorganisms.

A necessary condition for the emergence and development of microorganisms is the presence of carbon source in a given environment (e.g., fuel tanks, pipelines, gas storage, gas supply systems, etc.). The deterioration of crude oil and petroleum products under the influence of microbial activity reduces the hydrocarbon content because they are being used as a carbon source in both aerobic and anaerobic conditions.

Another essential and necessary condition for the growth of microorganisms in oil or products of its processing is the presence of water in the production well, accumulation of water in the pipelines during transmission or at the bottom of the tanks during storage. The existence of the possibility of interactions between oil and water adds complexity of the issue of Microbial Contamination, Microbial Influenced Corrosion and biofilm creation.

Bacteria and fungi are two main groups of microorganisms that contaminate fuel production process. Both bacteria and fungi require food and water to thrive. In a fuel oil storage tank their "food" is the oil. They get water from the water that collects at the bottom of the storage tank and get food from the fuel-water interface. The resulting microbial slimes (biofilms) are from the unchecked growth of these microorganisms that are always present in air, fuel, and water. Microorganisms will degrade fuels and fuel systems if left unmitigated.

MC, MIC and Biofilms

Microbial Contamination (MC), Microbial Influenced Corrosion (MIC) and/or biofilm formation is frequently observed at oil production sites and in transport pipelines, and among other types of equipment involved in the oil production industry.

The mechanisms by which Microbial Contamination (MC), Microbial Influenced Corrosion (MIC) and/or biofilm creation causes damage are not fully understood despite many decades of research. However, Microbial Contamination (MC), Microbial Influenced Corrosion (MIC) and/or the biofilms created pose severe operational, environmental, and safety problems to the petroleum and/or natural gas industries, particularly with respect to contamination in hydrocarbons and corrosion of equipment used in the storage, processing, and/or transport of oil and gas crude and/or processed materials. Costs resulting from MC and MIC in these industries due to repair and replacement of damaged equipment, spoiled oil, environmental clean-up, and injury-related health care, amount to well over several billion USD per year, posing a major economic problem for the mining and refining industry, as well as a huge threat to the environment.

Development and metabolic activity of microflora directly leads to the deterioration of the physico-chemical parameters of oil and fuel. A negative phenomenon is the precipitation of biomass (sludge), which are metabolic products of fungi, bacteria, yeast, etc. The biomass, or sludge, forms larger agglomerates. This causes the silting of reservoir rocks, clogging of pipelines, and accumulation of sediments at the bottom of fuel tanks. Bacterial contamination is usually observed in crude oil, whilst fungi usually cause contamination of aviation fuel. The number of microorganisms (bacteria and fungi) in the aqueous layer contained in crude oil and petroleum products, determines the amount of contamination.

Also, Microbial Contamination and Microbial Influenced Corrosion leads to additional corrosion, often characterized by or with pitting of metal surfaces caused by sulfate-reducing bacteria, and frequently results in extensive damage to oil and gas storage, production, and transportation equipment. Pipe systems, tank bottoms, and other pieces of oil production equipment can rapidly fail if there are areas where microbial corrosion is occurring. If a failure occurs in a pipeline or oil storage tank bottom, the released oil can have serious environmental consequences. More crucially, if a failure occurs in a high-pressure water or gas line, the consequences may be worker injury or death. Any failure at least involves significant repair or replacement costs.

There are several stages during which microbiological contamination of oil, gas and their derivatives may occur. In the initial stages of growth, the organisms present are predominantly aerobic, using the dissolved oxygen in the water for respiration. As this supply of oxygen is depleted, anaerobic bacteria (typically known as sulfate-reducing bacteria) develop. These organisms do not require oxygen for respiration and form corrosive waste products. One waste expelled by the organisms is hydrogen sulfide. Sulfate-reducing bacteria also use the enzyme hydrogenase, which scavenges hydrogen ions from the metallic surfaces beneath biofilms. Hydrogenase activity accelerates galvanic corrosion. Other anaerobic bacteria growing produce weak organic acids. The weak organic acids react readily with chloride, nitrate, nitrite, and sulfate anions to form strong inorganic acids, which attack infrastructure surfaces.

The microorganisms thought to be primarily responsible for corrosion at least in an anaerobic environment within the oil industry are sulfate-reducing bacteria. Other culpable bacteria include iron-oxidizing bacteria, sulfur-oxidizing bacteria, nitrate reducing bacteria, methanogens, and acid producing bacteria, among others. These categories of bacteria generally are capable of reducing metal directly, producing metabolic products that are corrosive and/or leading to the formation of biofilms that indirectly alter the local environment to promote corrosion and sludge formation.

Sulfate-reducing bacteria, in particular, are ubiquitous and can grow in almost any environment. They are routinely found in waters associated with oil production systems and can be found in virtually all industrial aqueous processes, including cooling water systems and petroleum refining. Sulfate-reducing bacteria require an anaerobic (oxygen-free) aqueous solution containing adequate nutrients, an electron donor, and an electron acceptor. A typical electron acceptor is sulfate, which produces hydrogen sulfide upon reduction. Hydrogen sulfide is a highly corrosive gas and reacts with metal surfaces to form insoluble iron sulfide corrosion products. In addition, hydrogen sulfide partitions into the water, oil, and natural gas phases of produced fluids and creates a number of serious problems. For instance, "sour" oil or gas, which contains high levels of hydrogen sulfide, has a lower commercial value than low sulfide oil or gas. Removing biogenic hydrogen sulfide from sour oil and gas increases the cost of these products. It is also an extremely toxic gas and is immediately lethal to humans at even small concentrations. Thus, its presence in the oil fields poses a threat to worker safety.

It is believed that Microbial Contamination and Microbial Influenced Corrosion are primarily caused by the formation of microbial biofilms in equipment that comes into contact with crude and gas oil and gas and/or the liquid systems involved in their storage, transport and/or refinement.

Biofilms and Treatable Surfaces

Microorganisms present in aqueous environments form biofilms on surfaces. Biofilm consists of populations of microorganisms and their hydrated polymeric secretions. Numerous types of organisms may exist in any particular biofilm, ranging from strictly aerobic bacteria at the water interface to anaerobic bacteria such as sulfate-reducing bacteria (SRB) at the oxygen depleted metal surface.

Biofilm formation is thought to follow a multi-series of specific steps that include: (a) an initial bacterial attachment stage that is rapid and reversible; (b) a longer termed attachment stage; (c) a replication phase; (d) a polysaccharide-rich matrix secretion stage; (e) a biofilm maturation stage; and (f) finally, a bacterial dispersal stage. Biofilms can be microns of millimeters to centimeters or more in thickness and can develop over the course of hours, days, or months, depending on many factors that include the consortium of bacteria present and the environment.

Biofilms are highly complex, naturally occurring biotic structures which have a wide range of characteristics. Their exact role in corrosion is still under intense study. However, biofilm-associated corrosion is at least a function of the composition of the underlying bacterial population that forms the biofilm and on the environment. The presence of biofilm can contribute to corrosion in at least three ways: (1) physical deposition, (2) production of corrosive byproducts, and (3) depolarization of the corrosion cell caused by chemical reaction.

Many of the byproducts of microbial metabolism, including organic acids and hydrogen sulfide, are corrosive. These materials can concentrate in the biofilms, causing accelerated metal attack and corrosion. Corrosion tends to be self-limited due to the buildup of corrosion reaction products. However, microbes can absorb some of these materials in their metabolism, thereby removing them from the anodic and cathodic sites. The removal of reaction products, termed depolarization, stimulates further corrosion.

Biofilms are usually found on solid substrates submerged in or exposed to an aqueous solution, although they can form as floating mats on liquid surfaces and also on the surface of debris, particularly in high humidity climates. Given sufficient resources for growth, a biofilm will quickly grow to be macroscopic. Biofilms can contain many different types of microorganism, e.g., bacteria, archaea, protozoa, fungi and algae; each group performs specialized metabolic functions. However, some organisms will form single species films under certain conditions. The social structure (cooperation, competition) within a biofilm highly depends on the different species present.

Biofilms are held together and protected by a matrix of secreted polymeric compounds called EPS. EPS is an abbreviation for either extracellular polymeric substance or exopolysaccharide, although the latter one only refers to the polysaccharide moiety of EPS. In fact, the EPS matrix consists not only of polysaccharides but also of proteins (which may be the major component in environmental and wastewater biofilms) and nucleic acids. A large proportion of the EPS is more or less strongly hydrated; however, hydrophobic EPS also occur; one example is cellulose which is produced by a range of microorganisms. This matrix encases the cells within it and facilitates communication among them through biochemical signals as well as gene exchange. The EPS matrix is an important key to the evolutionary success of biofilms and their resistance to, in this case, biocides and other chemical treatments to remove them. One reason is that it traps extracellular enzymes and keeps them in close proximity to the cells. Thus, the matrix represents an external digestion system and allows for stable synergistic micro consortia of different species. Some biofilms have been found to contain water channels that help distribute nutrients and signaling molecules.

Despite these protective physical and biological properties of biofilms and in particular, the EPS which presents a significant permeability barrier to antibacterial agents, oxidizing agents (and oxidizing agent analogs) has been shown by the inventor to be effective in mitigating the formation of biofilms on metal surfaces, in particular, under anaerobic conditions.

Biofilms that form in the hydrocarbons or on the surfaces of such metal components are thought to be the primary causative agent triggering corrosion. Many biofilm-forming environmental bacteria, particularly those in anaerobic environments, produce harmful gases (e.g., hydrogen sulfide), acids (e.g., sulfuric acid), and other agents which are highly corrosive and also which pose health and safety concerns to those workers in the industry. Currently, mitigation techniques to reduce microbial induced corrosion are available but are not often effective enough and/or are not practical in the industry due to high cost, limited efficacy and other reasons. For example, the use of current biocides is common, but their effectiveness is limited due to inability to permeate the corrosive biofilms.

EMODs and Synergistic Chemical Reaction

As shown in exemplary embodiments herein, oxidizing agent compositions and compounds that are functionally equivalent to oxidizing agents, when combined with radiation of certain wavelengths, may significantly reduce microbial concentration and/or formation of biofilms. Consequently, such compositions and compounds may be used to reduce, mitigate, or eliminate Microbial Contamination in hydrocarbons and/or Microbial Influenced Corrosion on metal surfaces, and in particular, metal surfaces on equipment involved in the storage, transport, and refinement in the petrochemical and natural gas industries.

The interest in environmentally friendly, non-toxic and degradable yet potent biocides has never been so high. Oxidizing agents have been extensively used as such biocides, particularly in applications where its decomposition into non-toxic byproducts is important. The majority of studies investigating the microbe toxic mechanism of oxidizing agents consider them as a source of oxidative stress in the cell to model chronic oxidative damage to cells. When used to treat microbes, oxidizing agents exhibit non-resistant characteristics, and thus have broad-spectrum antibacterial and antimicrobial effects. Oxidizing agents, notably hydrogen peroxide ($H_2O_2$), are increasingly used in a number of medical, food and industrial applications but also in environmental applications.

Electronically modified oxygen derivatives (EMODs) are chemically reactive chemical species containing oxygen. Examples of EMODs include peroxides, superoxide, hydroxyl radical, and singlet oxygen. EMODs may serve as an antimicrobial defense. Individuals with chronic granulomatous disease who have deficiencies in generating EMODs, are highly susceptible to infection by a broad range of microbes including *Salmonella enterica, Staphylococcus aureus, Serratia marcescens,* and *Aspergillus* spp. A role for EMODs in antiviral defense mechanisms also can be demonstrated via Rig-like helicase-1 and mitochondrial antiviral signaling protein. Increased levels of EMODs potentiate signaling through this mitochondria-associated antiviral receptor to activate interferon regulatory factor (IRF)-3, IRF-7, and nuclear factor kappa B (NF-κB), resulting in an antiviral state.

EMODs may be generated through a synergistic chemical reaction of oxidizing agents and ionizing/nonionizing radiation. During the process that the radiation and the oxidizing agents interact, damaging intermediates may be created. Oxidizing chemicals may be used as the precursors to EMODs, while the radiation may function as an exogenous source. This type of synergistic reaction may lead to a situation where the resulted antimicrobial effect is much greater than the sum of the effect caused by individual components of the reaction.

In the synergistic reaction process, water loses an electron and becomes highly reactive. Then through a three-step chain reaction, water is sequentially converted to hydroxyl radical (.OH), hydrogen peroxide ($H_2O_2$), superoxide radical ($.O^{-2}$) and ultimately oxygen ($O_2$). The hydroxyl radical is extremely reactive and immediately removes electrons from any molecule in its path, turning that molecule into a free radical and thus propagating a chain reaction. Actually, hydrogen peroxide is even more damaging to DNA of microbes than the hydroxyl radical, because the lower reactivity of hydrogen peroxide provides enough time for the molecule to travel into the nucleus of the cell, subsequently reacting with macromolecules such as DNA.

This discovery may find application in reducing microbial concentration. As an example, a 3% solution of hydrogen peroxide can be expected to eliminate approximately 30% of microbes that are exposed to it. Radiation of a wavelength between 300 nanometers and 600 nanometers can be expected to eliminate 3% of the microbes exposed to it. However, when 3% hydrogen peroxide and radiation of a wavelength between 300 nanometers and 600 nanometers are administered together, the resulted synergistic reaction may eliminate 99.999% of microbes exposed to the combination.

Also, this discovery may find application in elimination and reduction of bacterial biofilms. In an example, a biofilm of bacteria was exposed to light of wavelengths of 300 to 600 nm for 30 to 60 seconds while in the presence of 3 to 300 mM of an oxidizing agent. Microbial counts from each treated sample were compared with those of the control samples. The results showed that the combination of the light and oxidizing agent successfully penetrated all layers of the biofilm, creating an excellent antibacterial effect. The ability of noncoherent light in combination with the oxidizing agent to affect bacteria in deep layers of biofilm illustrates that this treatment may be applied in biofilm-related Microbial Contamination, Microbial Influenced Corrosion and biofilm elimination as a minimally invasive antibacterial procedure.

Combination of Oxidizing Agent Compositions and Radiation

Compositions containing oxidizing agents may be administered together with radiation of certain lengths to hydrocarbons, typically oil and gas, or surfaces in need of treatment for the effective mitigation and/or elimination of microbes and biofilms, and particularly, microbes and biofilms in anaerobic conditions. Exemplary embodiments shown and described herein show that oxidizing agents and compounds that are functionally equivalent to oxidizing agents can form a synergistic reaction when combined with radiation of certain wavelengths. In particular embodiments, such combination of oxidizing agent compositions and radiation may significantly reduce microbial concentration in the target hydrocarbon and/or reduces the formation of biofilms on liquid surfaces and on equipment, and consequently may be used to reduce, mitigate, or eliminate Microbial Contamination and/or Microbial Influenced Corrosion on metal surfaces, in particular, metal surfaces on equipment involved in the storage, transport, and refinement in the oil, petrochemical and natural gas industries. Such equipment may be pipelines, storage tanks, and the refinement processing equipment.

In some embodiments, the oxidizing composition in combination with radiation may be extremely effective in reducing, eliminating, or blocking biofilm formation in anaerobic environments, which was not previously known or appreciated.

Oxidizing agents may be those synthesized by a variety of methods. Oxidizing agents and their derivatives may be obtained commercially from a wide range of sources that will be known by the skilled artisan. Oxidizing agents may also be naturally occurring. Oxidizing agents are widely distributed in the natural environment and can be produced by a variety of bacteria. For example, oxidizing agents can be produced by bacteria as a degradation product. As an intercellular signal molecule, $H_2O_2$ regulates various aspects of bacterial physiology. Table 1 lists common oxidizing agents and their corresponding products as non-limiting examples.

TABLE 1

| Oxidizing Agents | Product(s) |
|---|---|
| oxygen ($O_2$) | Various products, including the oxides $H_2O$ and $CO_2$ |
| ozone ($O_3$) | Various products, including ketones, aldehydes, and $H_2O$; see ozonolysis |
| fluorine ($F_2$) | $F^-$ |
| chlorine ($Cl_2$) | $Cl^-$ |
| bromine ($Br_2$) | $Br^-$ |
| iodine ($I_2$) | $I^-, I^-_3$ |
| hypochlorite ($ClO^-$) | $Cl^-, H_2O$ |

TABLE 1-continued

| Oxidizing Agents | Product(s) |
|---|---|
| chlorate ($ClO^-_3$) | $Cl^-$, $H_2O$ |
| nitric acid ($HNO_3$) | nitric oxide (NO) |
| $NO_2$ | nitrogen dioxide |
| $SO_2$ (sulfur dioxide) | sulphur (ultramarine production, commonly reducing agent) |
| Hexavalent chromium | $Cr^{3+}$, $H_2O$ |
| $H_2O_2$, other peroxides | Various products, including oxides and $H_2O$ |

The disclosed invention also contemplates the use of oxidizing agent analogs or equivalent compounds. "Oxidizing agent equivalent" or "oxidizing analog or functionally equivalent compound, molecule or derivative" or similar terms may include any known or yet unknown compounds that have a structure that is similar to oxidizing agents to a degree such that they can produce the same or similar biological effects as oxidizing agents. Such analogs or functionally equivalent compounds may be obtained in various ways, including isolation from nature, chemical modification, or via chemical synthesis.

In certain embodiments, the oxidizing agent compositions combined with radiation for use in the exemplary methods may be prepared to have any useful properties that may be appropriate or advantageous to the particular substance or surface to be treated. The exact ingredient of the oxidizing agent compositions may depend on various factors, e.g., whether the substance/surface to be treated is under aerobic or anaerobic conditions, the pH and salinity of the substance/surface to be treated, the consortium or population characteristics of the bacteria present in the biofilm of the target substance/surface to be treated, the properties of the biofilm to be treated, among other characteristics.

The oxidizing agent compositions combined with radiation may also include components that may help stabilize and/or improve the oxidizing agents as the active ingredient, or components that may facilitate delivery of the oxidizing agents. For example, the oxidizing agent compositions herein described may also include surfactants or disruption agents and the like which may increase the permeability and/or disruption of the biofilm to facilitate the movement of the oxidizing agent composition into the biofilm and into contact with the bacteria therein.

Surfactants are well known in the art and include anionic surfactants (e.g., ammonium lauryl sulfate, sodium lauryl sulfate (SDS, sodium dodecyl sulfate, another name for the compound), sodium lauryl ether sulfate (SLES), and sodium myreth sulfate; sodium stearate, sodium lauroyl sarcosinate), cationic surfactants (Octenidine dihydrochloride, Cetylpyridinium chloride (CPC), Benzalkonium chloride (BAC), Benzethonium chloride (BZT), 5-Bromo-5-nitro-1,3-dioxane, Dimethyldioctadecylammonium chloride, Cetrimonium bromide, Dioctadecyldimethylammonium bromide (DODAB)), and nonionic surfactants (Polyoxyethylene glycol alkyl ethers, Polyoxypropylene glycol alkyl ethers, Glucoside alkyl ethers, Polyoxyethylene glycol octylphenol ethers (e.g., Triton-X), Polyoxyethylene glycol alkylphenol ethers, Glycerol alkyl esters, Polyoxyethylene glycol sorbitan alkyl esters, Polyethoxylated tallow amine (POEA)), as well as biosurfactants (surface active substances synthesized by living cells).

When administering the oxidizing agent composition in combination with radiation to a site targeted for treatment (e.g., a surface having MIC or a substance having MC), the composition may be administered or delivered in an amount or dosage sufficient to provide an effective amount of the oxidizing agent composition in combination with radiation or oxidizing agent composition analog in combination with radiation. The term "effective amount of the oxidizing agent or oxidizing agent analog" is the minimal amount, level, or concentration of the oxidizing agent or oxidizing agent analog which results in a measurable or detectable effect on the substance or metal surface to be treated, in particular, on the MC, MIC or the associated biofilm itself. The effective amount can be measured in terms of concentration as parts-per-million (ppm), percentages or any suitable measurement.

In certain embodiments, the effective amount of the oxidizing-agent-containing compositions provides a concentration of the oxidizing agent compound that is between about 0.001 percent to 50 percent or more of the volume of the hydrocarbon to be treated. However, it will be clear to a person skilled in the art that this term may refer to any suitable concentration that is necessary to achieve the desired effects.

Although any treatment methods similar or equivalent to those described herein can also be used in the practice or testing of the present disclosure, some exemplary methods are now described.

Treatment Methods and Applications

As shown in the exemplary embodiments, the combination of oxidizing agents and radiation of certain wavelengths may form a synergistic reaction. The synergistic reaction may generate EMODs, which may be effective in reducing microbial count and eliminating or blocking biofilm formation, particularly in anaerobic environments. Prior to the invention described in this disclosure, this synergistic reaction involving oxidizing agents and radiation of certain wavelengths was not known or appreciated as to its relationship to EMOD creation or its effect on Microbial Contamination (MC), Microbial Influenced Corrosion (MIC) or biofilm creation. MC, MIC and biofilm may be eliminated or greatly reduced with the disclosed treatment methods in or on equipment including pipelines, storage tanks, and refinery processing equipment.

In one aspect, the embodiment may relate to a method for reducing microbial concentration or for reducing biofilm formation to mitigate or eliminate Microbial Contamination and/or Microbial Influenced Corrosion on a metal surface. The method may include contacting the substance or metal surface to be treated with an effective amount of a liquid composition comprising an oxidizing agent or a functionally equivalent analog or derivative thereof, and exposing the resulted mixture of the substance or metal surface to be treated and the liquid composition to radiation of certain wavelengths. The oxidizing agent and the radiation together form a synergistic reaction, resulting in an antimicrobial effect that is stronger than the sum of that of the oxidizing-agent-based composition and radiation when acting separately. In other aspects, the disclosure may relate to corresponding combination and device for reducing microbial concentration or for reducing biofilm formation to mitigate or eliminate Microbial Contamination and/or Microbial Influenced Corrosion on a metal surface.

The method disclosed herein may also include additional upstream and/or downstream testing steps that facilitate knowing whether and how to administer the treatment involving an oxidizing agent composition combined with radiation of certain wavelengths. Such additional steps may aim to determine whether a target system has a legitimate MC and/or MIC risk at a particular site (e.g., a crude pipeline that transports crude oil from an offshore rig to a distant domestic refinery). Other steps may also involve subsequent monitoring steps to evaluate the extent of the MC and MIC associated biofilm, followed then by steps to carry out a particular treatment plan of the oxidizing agent composition compound combined with radiation of certain wavelengths, e.g., an aggressive treatment plan or a lower strength treatment plan.

For example, corrosive damage to a pipeline may be detected as a result of regularly scheduled maintenance along a certain ten-mile stretch of crude oil pipeline. In order to learn more about the extent and nature of the damage, and therefore to determine an appropriate treatment, a user may sample the environmental conditions at various points along the pipeline by assessing properties that would be indicative of conditions suitable for biofilm formation, including, but not limited to: (a) detection of certain bacterial species known to have a role in bacterial corrosion (e.g., sulfate reducing bacteria), (b) detection of certain corrosive metabolites (e.g., presence of organic acids, hydrogen sulfide gas, or the like), (c) existence of suitable pH and temperature conditions known to be supportive of biofilm development, (d) presence of an aqueous environment (e.g., extent of water dropout or separation of a water phase from the crude oil), (e) slow flow rate (which is known to be conducive to biofilm formation), and (f) existence of high bacterial biomass. The person of ordinary skill may also wish to examine physical samples collected from the pipeline wall to detect and characterize the biofilm (e.g., thickness) or metal coupon samples placed into the flow path. Such factors may be evaluated and then assessed by the skilled person to design a specifically tailored oxidizing agent compound combined with radiation of certain wavelengths, resulting in a synergistic-reaction-based treatment.

In some embodiments, variables affecting the specific nature of any given synergistic-reaction-based treatment involving oxidizing agent compounds combined with radiation of certain wavelengths may include, for example: (a) pH of the oxidizing agent compound composition, (b) salinity of the oxidizing agent compound composition, (c) concentration of the oxidizing agent compound in the liquid composition (e.g., 1%, 2%, 5%, 10%, 50%, w/v), (d) target or desired concentration of the oxidizing agent compound composition once delivered in the flow path (e.g., 1 ppm, 2 ppm, 4 ppm, 10 ppm, 50 ppm, 100 ppm, 500 ppm, 1000 ppm or more), (e) the rate of hydrocarbon flow, (f) the rate of injection of the oxidizing agent compound composition, (g) the types of bacteria present in the consortium of the biofilm, (h) the level of bacterial biomass and/or biofilm present, (i) the presence of visible evidence of corrosion (e.g., pits) (which generally is associated with the degree of corrosion in an increasing linear relationship), and (j) the detection of metal loss on test coupons. Each of these factors may be assessed, along with other available factors, to gauge the severity of the MC and MIC risk and/or the degree of biofilm associated corrosion. Once the severity of the corrosion is known, the skilled person can determine the best course for administering the treatment (i.e., the oxidizing agent compound composition combined with radiation of certain wavelengths).

Treatment may be aggressive in nature, or otherwise less aggressive, depending on the degree and severity of the MC and/or MIC and/or biofilm formation. For example, if the degree of biofilm associated corrosion is determined to be low, a gentle treatment may be administered by, for example, reducing the total amount or concentration of the oxidizing agent compound composition combined with radiation of certain wavelengths delivered, reducing the number of hours of continued injection into the site of interest, or increasing the number of days spanning between follow-up injections. However, if the degree of biofilm associated corrosion is determined to be high, a more aggressive treatment may be administered by, for example, increasing the total amount or concentration of the oxidizing agent compound combined with radiation of certain wavelengths delivered, increasing the time period for continuous injection, or shortening the number of time or days between successive treatments.

The oxidizing-agent-based compositions combined with radiation of certain wavelengths of the disclosure may be used to treat any affected surface, and in particular, any affected metal surface on any equipment involved in the storage, transport, and/or refinement of petroleum and/or natural gas products. For example, affected surfaces may include a pipeline that transports crude oil from onshore or offshore drill site or from hydraulic fracturing sites to local or distant petroleum and/or natural gas refineries. Problematic biofilms may form along the interior surfaces of pipelines over distances that extend over many miles or tens of miles, leading to corrosive conditions over a multitude of points. It is generally accepted that pipeline corrosion represents the majority of corrosive damage due to MC and MIC in the oil and gas industries, particularly given that there are over 190,000 miles of liquid pipelines in the US alone. In another example, affected surfaces may include oil storage facilities at refinery sites or those located on oil transport tankers. Other equipment, such as pumps, valves, and other equipment that comes into contact with the oil flow path, is susceptible to the formation of biofilms and thus to MC and MIC. Any and all of these sites and surfaces may be treated using the methods disclosed herein.

Figure 1:
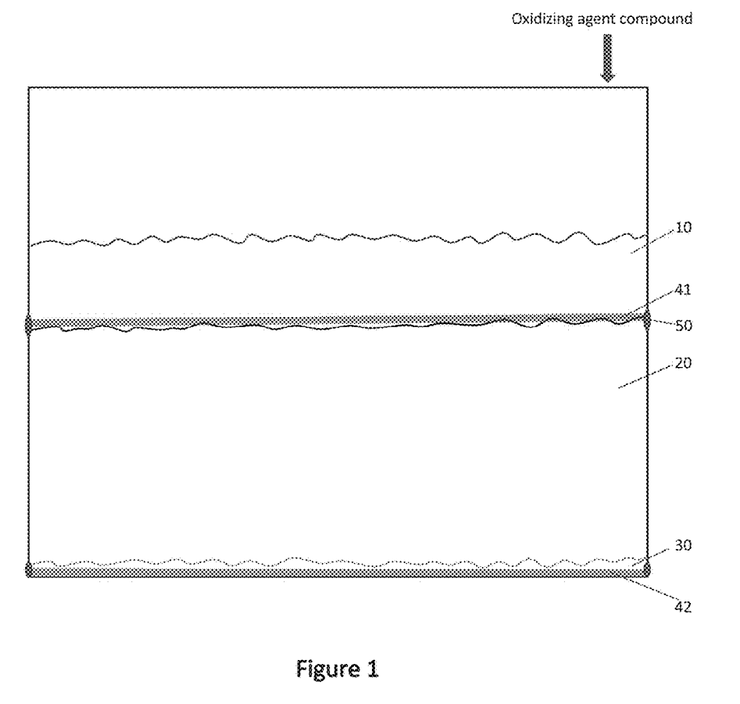
FIG. 1 depicts a diagram showing an exemplary embodiment in which a method is applied in a storage tank of gas, oil or other petrochemical product with less density than water.

Exemplary FIG. 1 depicts a diagram showing an embodiment in which the method is applied in a storage tank of oil. It will be understood by one skilled in the art that this exemplary embodiment can be used in a storage tank of gas, or other petrochemical raw materials, or refined products, as desired. As illustrated in FIG. 1, water 10 is accumulated on the bottom of the tank during storage of oil 20. Oil 20 has a density or specific gravity less than that of water, and thus floats on the surface of water 10. Typically, bacteria and/or fungi that invade the tank thrive at the interface between the oil layer and the water layer, obtaining water from water 10 while obtaining hydrocarbons as "food" from oil 20. Also, the greatest Microbial Contamination (MC) normally occurs at the oil-water interface because the bacterial life is well supported there. Moreover, at the locations 50 where the oil-water interface touches the metal tank, the greatest Microbial Influenced Corrosion (MIC) may be observed. The rapid growth of the microorganisms such as fungi, bacteria, yeast at the oil-water interface not only leads to formation of corrosive biofilms, their metabolic products may further form larger agglomerates, causing precipitation of sludge 30 on the bottom of the tank. Microbial Influenced Corrosion (MIC) may be observed at the locations where sludge 30 touches the metal tank as well.

In the method according to this exemplary embodiment, an effective amount of the liquid composition comprising the oxidizing agent compound or a functionally equivalent analog or derivative thereof may be administered into the oil. In certain embodiments, the effective amount of liquid composition may be administered into the water that exists in the tank. Because the microbes require water to survive and multiply, treating the water with the oxidizing agent while exposing the mixture to certain wavelengths of radiation creates EMODs that reduce or eliminate the MC, MIC and/or biofilm. In some embodiments, the liquid composition comprising the oxidizing agent compound may be introduced into the tank via a pump. In other embodiments, the oxidizing-agent-based liquid composition may be introduced manually.

A radiation emission mat 41 may be arranged inside the storage tank, near to the target areas to be treated. A typical target area may be the oil-water interface. With its density or specific gravity properly designed, the radiation emission mat 41 can be kept in the storage tank at a desired location, e.g., floating at the oil-water interface, suspended from an anchor element above the storage tank or above the desired location of disposal of mat 41, supported and held in place by an anchor element at or near a bottom portion of a storage tank, or otherwise fixed in place in the storage tank through any fixing elements, as desired. The radiation emission mat 41 may emit radiation of certain wavelengths, e.g., a wavelength between 300 nm and 600 nm. In certain embodiments, the radiation emission mat 41 is movable so that it may be controlled to stay at a desired location relative to the target areas. The wavelength, intensity and/or time of duration of the radiation emitted from the mat 41 also may be adjustable, for example a wavelength between 300 nm and 600 nm.

Figure 2:
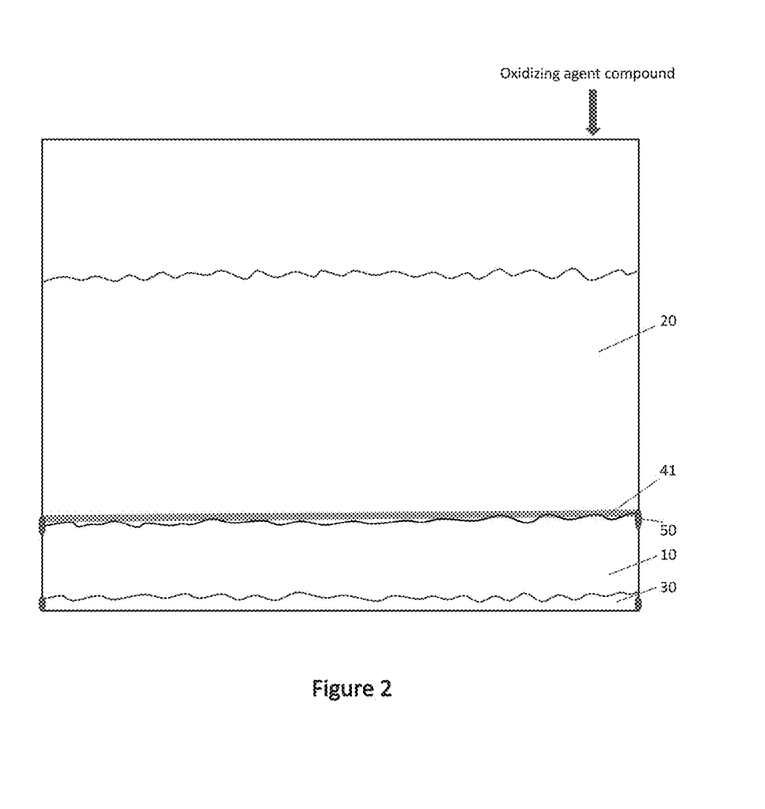
FIG. 2 depicts a diagram showing an exemplary embodiment in which a method is applied in a storage tank of gas, oil or other petrochemical product with greater density than water.

FIG. 2 depicts a diagram showing another exemplary embodiment in which the method is applied in a storage tank of oil. The present embodiment can also be used in a storage tank of gas or other petrochemical raw materials or refined products, as desired. As illustrated in FIG. 2, oil 20 has a density or specific gravity greater than that of water, and thus water 10 that is accumulated in the storage tank is floating on the surface of oil 20. Similarly, the greatest Microbial Contamination (MC) may be observed at the oil-water interface, and the greatest Microbial Influenced Corrosion (MIC) at the locations 50 where the oil-water interface touches the metal tank. Microbial Influenced Corrosion (MIC) may be observed at the locations where sludge 30 touches the metal tank as well.

Oxidizing agent compounds may be similarly introduced into the storage tank manually or via a pump. At least one radiation emission mat may be arranged inside the tank, near to the target areas to be treated. The target areas may include, but are not limited to, the oil-water interface and the bottom of the storage tank. In certain embodiments, with their density or specific gravity properly designed, a radiation emission mat 41 may be arranged floating at the oil-water interface, while a second radiation emitting mat 42 may be provided as resting on the bottom of the storage tank, near to sludge 30. The radiation emission mats 41 and 42 may emit radiation of certain wavelengths, for example a wavelength between 300 nm and 600 nm.

Figure 3:
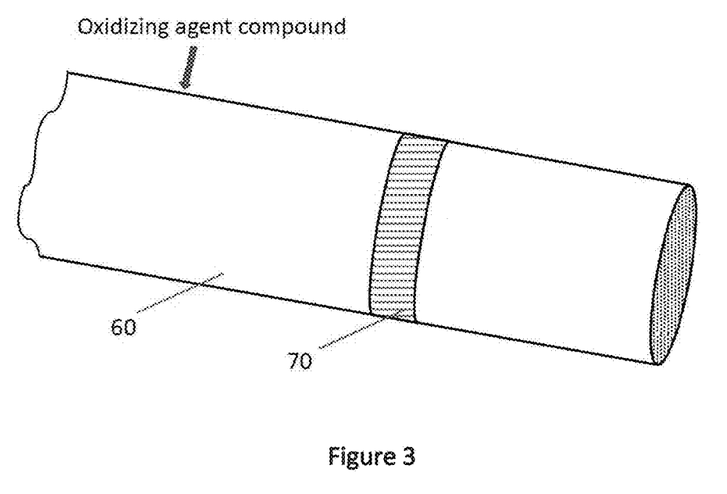
FIG. 3 depicts a diagram showing an exemplary embodiment in which a method is applied in a length of pipeline of gas, oil or other petrochemical product.

Exemplary FIG. 3 depicts a diagram showing an embodiment in which the method is applied in a length of pipeline of oil. The present embodiment may be used in a length of pipeline of gas or other petrochemical raw materials or refined products, as desired. In this embodiment, a band 70 with radiation producing function may be arranged inside the pipeline 60, in the form of a lining layer on the wall of the pipeline 60. An effective amount of a liquid composition comprising an oxidizing agent compound or a functionally equivalent analog or derivative thereof may be administered into the pipeline 60. The radiation producing band 70 may emit radiation of certain wavelengths, for example a wavelength between 300 nm and 600 nm.

In certain embodiments, various sensors may be provided to detect variables including, but not limited to, pH, temperature, density, oxygen concentration of the oil stored in the tank or transported through the pipeline. Further, the effective amount of the liquid composition comprising the oxidizing agent compound or a functionally equivalent analog or derivative thereof may be determined on the basis of any one or more of the density and light absorbing quality of the oil to be treated, and the size and shape of the container (tank, pipeline, or the like) thereof.

In certain embodiments, the formulation of the liquid composition may be determined on the basis of whether the oil to be treated is under aerobic or anaerobic conditions, pH of the oil, salinity of the oil, consortium or population characteristics of the microorganism present in the oil, the microbial content of the oil and/or the microbial content of the biofilms.

In certain embodiments, the wavelength, intensity, duration time and/or location relative to the oil to be treated, of the radiation, may be determined on the basis of any one or more of the density and light absorbing quality of the oil, the size and shape of the container thereof, whether the oil is under aerobic or anaerobic conditions, pH of the oil, salinity of the oil, consortium or population characteristics of the microorganism present in the oil, and the microbial content of the biofilms.

In certain embodiments, the person of ordinary skill in the art will easily be able to assess the degree of biofilm associated corrosion or contamination based on various measurable inputs and accordingly determine a proper course of the oxidizing agent compound combined with a radiation of certain wavelengths without undue experimentation.

Combination Treatments

Exemplary embodiments shown and described herein relate, in part, to the discovery that oxidizing agents or compounds that are functionally equivalent may form a synergistic reaction together with radiation of certain wavelengths. The resulting synergistic reaction may result in a product that may significantly reduce the formation of microbes and biofilms in the hydrocarbons and on surfaces, and consequently, may be used to reduce, mitigate, or eliminate Microbial Contamination associated with the hydrocarbons and/or Microbial Influenced Corrosion on metal surfaces, in particular, metal surfaces on equipment involved in the storage, transport, and refinement in the petrochemical and natural gas industries. In particular embodiments, the product of the synergistic reaction involving the oxidizing agents and radiation may be effective in reducing, eliminating, or blocking microbes and biofilm formation in anaerobic environments, which prior to the disclosure was not known or appreciated. Such equipment can include pipeline, storage tanks, and refinery processing equipment.

The synergistic reaction associated with oxidizing agents and radiation methodologies herein disclosed may be advantageous over existing mitigation practices at least because: (a) the oxidizing agents may be a natural product of environmental bacteria, hence minimal environmental impact compared to currently available biocides; (b) current biocides are naturally taken up by bacteria in a biofilm and induce a switch to planktonic growth behavior (i.e., growth away from biofilm environment) and thus, lack biofilm permeability aspects needed to better eliminate MC and MIC; (c) this MC and MIC eliminating or reducing treatment may be compatible with commercial corrosion inhibitors, whereas many current biocides are not; (d) Further, the synergistic reaction between the oxidizing agents and the radiation presents no negative environmental impact which is unique compared with current methods of treating MC and MIC and this invention results in a more complete elimination or reduction in MC and MIC than currently available methods; and (e) the reduction in MC and MIC is significantly greater than currently available methods.

Moreover, the disclosed synergistic reaction treatment methods involving oxidizing agent compound combined with radiation of certain wavelengths may be also contemplated to be combined with other MC and/or MIC mitigation strategies, such as the use of corrosion resistant metals, temperature control, pH control, radiation, filtration, protective coatings with corrosion inhibitors or other chemical controls (e.g., biocides, oxidizers, acids, alkalis), bacteriological controls (e.g., phages, enzymes, parasitic bacteria, antibodies, competitive microflora), pigging (i.e., mechanical delamination of corrosion products), sonication, stirring (the introduction of movement in the substance to be treated), anodic and cathodic protection, and modulation of nutrient levels.

For instance, in certain embodiments relating to pipeline treatment, the pipeline may be first treated with pigging. The pigging can help not only to physically remove the biofilm, but also acts to disturb the biofilm such that the permeation of the biofilm is improved, thereby rendering the synergistic reaction treatment involving oxidizing agent compounds combined with radiation of certain wavelengths more effective. Methods and equipment for pigging pipelines are well known in the art and thus are not described in detail here.

EXAMPLES

This disclosure may be further demonstrated by the following examples which should not be construed as limiting. The contents of all references, including any publicly available polypeptide and/or nucleic acid sequences accession numbers (e.g., GenBank), and published patents and patent applications cited throughout the application are hereby incorporated by reference Persons of ordinary skill in the art will recognize that the disclosure may be practiced with variations on the disclosed structures, materials, compositions and methods, and such variations are regarded as within the ambit of the disclosure.

Example 1

Example 1 may demonstrate reduction of MC and MIC associated with DvH growing on carbon steel in the presence of oxidizing agent compounds combined with radiation of certain wavelengths which may result in a synergistic reaction.

In Example 1, carbon steel coupons were incubated in the presence of O and oxidizing agent compounds, combined with radiation of certain wavelengths in a synergistic reaction, with and without an inoculum of DvH. The metal loss of the carbon steel coupons was measured. The results show that coupons incubated with DvH experienced approximately a 2-fold more weight loss than those incubated in a sterile environment. Additionally, the data shows that oxidizing agent compounds combined with radiation of certain wavelengths in a synergistic reaction reduces and/or eliminates corrosion in the presence of DvH (MIC) compared to the no oxidizing agent compound combined with radiation of certain wavelengths in a synergistic reaction treatment, and that this reduction in weight loss is not replicated in a sterile environment without DvH inoculation. Therefore, the experiment demonstrates that oxidizing agent compounds combined with radiation of certain wavelengths in a synergistic reaction has inhibitory effect on corrosion is MIC specific.

Example 2

Example 2 may demonstrate that Microbial Contamination MC and Microbial Induced Corrosion (MIC) by DvH is reduced by different concentrations of an oxidizing agent compound combined with radiation of certain wavelengths in a synergistic reaction.

In example 2, steel coupons were incubated in cultures of DvH for three days with and without exposure to an oxidizing agent compound combined with radiation of certain wavelengths in a synergistic reaction and then the coupons were measured to determine the amount of metal loss due to corrosion. Coupons incubated in the absence of an oxidizing agent compound combined with radiation of certain wavelengths in a synergistic reaction resulted in nearly 2-fold more metal loss than the coupons grown in the presence of an oxidizing agent compound combined with radiation of certain wavelengths in a synergistic reaction. The data demonstrates that the metal coupons in the presence oxidizing agent compound combined with radiation of certain wavelengths in a synergistic reaction displayed little to no corrosion. Therefore, the experiment demonstrates that oxidizing agent compounds combined with radiation of certain wavelengths in a synergistic reaction inhibit corrosion of metal caused by anaerobic biofilms formed from sulfate-reducing bacteria.

Example 3

Example 3 may demonstrate the treatment of oil field pipeline with oxidizing agent compounds combined with radiation of certain wavelengths of in a synergistic reaction to inhibit Microbial Influenced Corrosion and associated biofilm formation In example 3, steel pipelines are used to transport seawater from treatment and pumping facilities to oil field water injection wells. The water is injected into specific regions of an oil-producing reservoir to provide secondary oil recovery. This provides additional oil recovery over that which results from primary, or natural, production due to the initial pressurization of the reservoir.

Treatment of the seawater prior to entering the pipeline is required to prevent corrosion of the steel pipeline and the steel tubing in the water injection wells and to improve injected water quality. The treatment process includes chlorination, filtration, deaeration, and addition of a solution of an oxidizing agent compound combined with radiation of certain wavelengths in a synergistic reaction. The chlorination kills the majority of the bacteria and algae entering the system with the water from the sea. The filtration removes most of the sea sediments, large particles, and biomass. Deaeration of the water is critical to remove oxygen, a key element involved in the corrosion process. Deaeration of the seawater to less than about 20 ppb oxygen essentially eliminates the potential for common oxygen-induced corrosion. Unfortunately, removing the oxygen results in an anaerobic environment, which increases the potential for anaerobic corrosion of the steel pipeline due to the activity of sulfate-reducing bacteria in the system and other categories of bacteria. Addition of a solution of an oxidizing agent (or functionally equivalent analog thereof) combined with radiation of certain wavelengths in a synergistic reaction will be introduced to control the activity of the corrosion inducing sulfate-reducing bacteria and other biofilm-forming bacteria that lead to corrosion, such as iron-oxidizing bacteria, sulfur-oxidizing bacteria, nitrate reducing bacteria, methanogens, and acid producing bacteria, among others.

EQUIVALENTS

The foregoing description and accompanying figures illustrate the principles, exemplary embodiments, and modes of operation of the invention. However, the invention should not be construed as being limited to the particular exemplary embodiments discussed above. Additional variations of the exemplary embodiments discussed above will be appreciated by those skilled in the art. Using no more than routine experimentation, one skilled in the art will recognize or be able to ascertain, many equivalents to the specific embodiments and methods described herein. Such equivalents are intended to be encompassed by the scope of the following claims.

Therefore, the above-described exemplary embodiments should be regarded as illustrative rather than restrictive. Accordingly, it should be appreciated that variations to those exemplary embodiments can be made by those skilled in the art without departing from the scope of the invention as defined by the following claims. For example, the relative quantities of the ingredients may be varied to optimize the desired effects, additional ingredients may be added, and/or similar ingredients may be substituted for one or more of the ingredients described. Additional advantageous features and functionalities associated with the methods, combinations and devices of the present disclosure will be apparent from the appended claims.

What is claimed is:

1. A method for reducing microbial concentration in a hydrocarbon or for reducing biofilms formed in a hydrocarbon, on the surface of the hydrocarbon, or on the surface of equipment involved in the storage, transport or processing of the hydrocarbon, comprising:
   introducing an effective amount of a liquid composition comprising an oxidizing agent compound into the hydrocarbon to be treated; and
   exposing the resulted mixture of the hydrocarbon and the liquid composition to radiation of certain wavelengths, wherein the liquid composition comprising the oxidizing agent compound functions together with the radiation of certain wavelengths to lead to a synergistic reaction.

2. The method of claim 1, wherein the radiation of certain wavelengths is radiation of a wavelength between 300 nanometers and 600 nanometers.

3. The method of claim 1, wherein the effective amount of the liquid composition provides a minimal amount of the oxidizing agent compound which results in a measurable or detectable effect on the microbial concentration or the biofilm formation.

4. The method of claim 3, wherein the effective amount of the liquid composition provides a concentration of the oxidizing agent compound that is between about 0.001 percent to 50 percent or more of the volume of the hydrocarbon to be treated.

5. The method of claim 1, wherein the effective amount of the liquid composition comprising the oxidizing agent compound is determined on the basis of any one or more of the density and light absorbing quality of the hydrocarbon to be treated, and the size and shape of the container thereof.

6. The method of claim 1, wherein the oxidizing agent compound is hydrogen peroxide, urea, carbamide peroxide, or benzoyl peroxide.

7. The method of claim 1, further comprising determining the formulation of the liquid composition on the basis of whether the hydrocarbon to be treated is under aerobic or anaerobic conditions, pH of the hydrocarbon, salinity of the hydrocarbon, consortium or population characteristics of the microorganism present in the hydrocarbon, the microbial content of the hydrocarbon and/or the microbial content of the biofilms.

8. The method of claim 1, wherein the liquid composition comprising the oxidizing agent compound further comprises at least one other inhibitor against Microbial Contamination in a hydrocarbon and/or Microbial Influenced Corrosion on a metal surface.

9. The method of claim 8, wherein the at least one other inhibitor is a biocide selected from the group consisting of germicides, antibiotics, antibacterials, antivirals, antifungals, antiprotozoals and antiparasites.

10. The method of claim 1, wherein the wavelength, intensity, duration time and/or location relative to the hydrocarbon to be treated, of the radiation, is determined on the basis of any one or more of the density and light absorbing quality of the hydrocarbon to be treated, the size and shape of the container thereof, whether the hydrocarbon is under aerobic or anaerobic conditions, pH of the hydrocarbon, salinity of the hydrocarbon, consortium or population characteristics of the microorganism present in the hydrocarbon, the microbial content of the hydrocarbon and the microbial content of the biofilms.

11. The method of claim 1, further comprising providing a secondary treatment for reducing microbial concentration or biofilm formation, which is selected from the group consisting of pigging, sonicization, radiation, filtration, stirring, bacteriological control, chemical control, temperature control, pH adjustment, nutrient adjustment, anodic and cathodic protection, protective coating with corrosion inhibitors, and installation of corrosion resistant metals.

12. The method of claim 1, wherein the effective amount of the liquid composition comprising the oxidizing agent compound is introduced into the water that exists where the hydrocarbon to be treated is collected, stored or transported.

\* \* \* \* \*